US012603162B2

(12) United States Patent
Singh

(10) Patent No.: US 12,603,162 B2
(45) Date of Patent: Apr. 14, 2026

(54) SYSTEM AND METHOD FOR AUTOMATIC DISPLAY OF CONTEXTUALLY RELATED DATA ON MULTIPLE DEVICES

(71) Applicant: INNOVACCER INC., San Francisco, CA (US)

(72) Inventor: Ishmeet Singh, Hayward, CA (US)

(73) Assignee: INNOVACCER INC., San Francisco, CA (US)

( * ) Notice: Subject to any disclaimer, the term of this patent is extended or adjusted under 35 U.S.C. 154(b) by 143 days.

(21) Appl. No.: 18/212,562

(22) Filed: Jun. 21, 2023

(65) Prior Publication Data

US 2023/0410962 A1 Dec. 21, 2023

Related U.S. Application Data

(60) Provisional application No. 63/354,164, filed on Jun. 21, 2022.

(51) Int. Cl.
*G16H 10/60* (2018.01)

(52) U.S. Cl.
CPC .................................. *G16H 10/60* (2018.01)

(58) Field of Classification Search
None
See application file for complete search history.

(56) References Cited

U.S. PATENT DOCUMENTS

| | | | |
|---|---|---|---|
| 6,408,294 B1 | 6/2002 | Getchius | ........... G06F 16/24534 |
| 6,484,161 B1 | 11/2002 | Chipalkatti | ............ G06Q 30/02 |

(Continued)

FOREIGN PATENT DOCUMENTS

| | | | |
|---|---|---|---|
| CN | 109508432 | 3/2019 | ........... G06F 16/955 |
| CN | 109871538 | 6/2019 | ............. G06F 17/27 |

(Continued)

OTHER PUBLICATIONS

Wilson, D., O'Sullivan, D., McLoughlin, E., & Bertolotto, M. (2006). Case-based decision support for intelligent patient knowledge management (Year: 2006).*

(Continued)

*Primary Examiner* — Emily Huynh

(74) *Attorney, Agent, or Firm* — HAYES SOLOWAY P.C.

(57) ABSTRACT

A system and a method for automatic display of contextually related information includes a first communication device, connected to first data sources, comprising a plurality of contextual information of a predetermined information type, stored therein. The first communication device includes a first application provided with a first application interface, communicatively connected to a backend server. The system further includes one or more second communication devices each comprising a secondary application provided with a second application interface, which are connected to second data sources having contextual information stored therein. The first application interface detects an access of a patient healthcare information and shares one or more context data with back-end server which in turn shares context data with second communication devices. The context data thus received at the second communication devices is utilized to visualize additional contextual information thereat.

8 Claims, 6 Drawing Sheets

(56) References Cited

U.S. PATENT DOCUMENTS

| | | | |
|---|---|---|---|
| 7,047,242 B1 | 5/2006 | Ponte | G06Q 10/00 |
| 7,611,466 B2 | 11/2009 | Chalana | A61B 8/0858 |
| 8,515,939 B2 | 8/2013 | Chen et al. | G06F 17/30 |
| 8,630,878 B1 | 1/2014 | Kravets et al. | G06Q 40/08 |
| 8,849,693 B1 | 9/2014 | Koyfman | G06Q 30/02 |
| 8,977,953 B1 | 3/2015 | Pierre | G06F 40/284 |
| 9,292,707 B1 | 3/2016 | Fontecchio | G06F 21/60 |
| 9,355,273 B2 | 5/2016 | Stevens | G06F 21/00 |
| 9,542,393 B2 | 1/2017 | Morton | G06F 16/7844 |
| 9,633,404 B2 | 4/2017 | Chawla et al. | G06F 7/04 |
| 9,727,591 B1 | 8/2017 | Sharma | G06F 16/215 |
| 9,830,476 B2 | 11/2017 | Fontecchio | H04L 9/32 |
| 10,056,078 B1 | 8/2018 | Shepherd | G06F 16/632 |
| 10,147,504 B1 | 12/2018 | Stettin et al. | G16H 50/30 |
| 10,366,346 B2 | 7/2019 | Achin et al. | G06F 15/18 |
| 10,514,949 B1 | 12/2019 | Korda | G06F 9/46 |
| 10,642,648 B2 | 5/2020 | Ling et al. | G06F 9/48 |
| 10,691,976 B2 | 6/2020 | Rogers et al. | G06K 9/62 |
| 10,789,373 B2 | 9/2020 | Reid et al. | G06F 21/60 |
| 10,810,223 B2 | 10/2020 | Sundararaman et al. | G06F 16/254 |
| 10,885,759 B1 | 1/2021 | Lee et al. | G08B 25/10 |
| 10,887,202 B2 | 1/2021 | Hutchison et al. | H04L 12/26 |
| 10,910,089 B2 | 2/2021 | Austin et al. | G06F 21/62 |
| 10,983,843 B2 | 4/2021 | Duggal et al. | G06F 9/54 |
| 11,474,836 B2 | 10/2022 | Awadallah et al. | G06F 9/448 |
| 11,670,422 B2 | 6/2023 | Basu et al. | G16H 50/70 |
| 11,682,041 B1 | 6/2023 | Xu et al. | G06Q 30/0201 |
| 11,687,940 B2 | 6/2023 | Muthuswamy et al. | G06Q 20/4016 |
| 11,783,260 B2 | 10/2023 | Fiumara et al. | G06N 5/04 |
| 2003/0018633 A1 | 1/2003 | Horn | G06F 17/18 |
| 2004/0215629 A1 | 10/2004 | Dettinger | G06F 16/2452 |
| 2005/0065956 A1 | 3/2005 | Brown | G06F 16/252 |
| 2005/0107902 A1 | 5/2005 | Blouin | G06Q 10/087 |
| 2005/0119534 A1 | 6/2005 | Trost | G06F 19/00 |
| 2005/0131778 A1 | 6/2005 | Bennett | G06F 10/0875 |
| 2006/0041539 A1 | 2/2006 | Matchett | G06Q 10/0639 |
| 2006/0075001 A1 | 4/2006 | Canning | G06F 8/65 |
| 2007/0239694 A1 | 10/2007 | Singh et al. | G06F 7/00 |
| 2007/0239724 A1 | 10/2007 | Ramer | G06F 16/951 |
| 2008/0147554 A1 | 6/2008 | Stevens et al. | H04L 9/00 |
| 2008/0263187 A1 | 10/2008 | Cascy et al. | G06F 15/173 |
| 2009/0012818 A1 | 1/2009 | Rodgers | G16H 10/65 |
| 2009/0112114 A1 | 4/2009 | Ayyagari et al. | A61B 5/08 |
| 2009/0313232 A1 | 12/2009 | Tinsley | G06Q 30/02 |
| 2010/0121879 A1 | 5/2010 | Greenberg | G06F 16/248 |
| 2010/0199169 A1 | 8/2010 | Gnech | G06F 16/972 |
| 2010/0287162 A1 | 11/2010 | Shirwadkar | G06F 16/3338 |
| 2011/0082712 A1 | 4/2011 | Eberhardt, III et al. | G16Z 99/00 |
| 2012/0083933 A1 | 4/2012 | Subbu et al. | G06F 1/26 |
| 2012/0253793 A1 | 10/2012 | Ghannam | G06F 17/27 |
| 2013/0054010 A1 | 2/2013 | Holman et al. | G06Q 50/01 |
| 2013/0054625 A1 | 2/2013 | Bhagwan et al. | G16H 10/60 |
| 2013/0054695 A1 | 2/2013 | Holman et al. | G09B 19/00 |
| 2013/0197936 A1 | 8/2013 | Willlich | G06Q 50/22 |
| 2013/0246290 A1 | 9/2013 | Courson et al. | G06F 40/205 |
| 2013/0325805 A1 | 12/2013 | Tochilnik | G06F 17/30 |
| 2014/0006061 A1 | 1/2014 | Watanabe | G06Q 30/02 |
| 2014/0149446 A1 | 5/2014 | Kuchmann-Beauger | G06F 17/30389 |
| 2014/0156315 A1 | 6/2014 | Canovi et al. | G06Q 40/08 |
| 2014/0188835 A1 | 7/2014 | Zhang | G06F 17/2705 |
| 2014/0344261 A1 | 11/2014 | Navta | G06F 16/605 |
| 2014/0350954 A1 | 11/2014 | Ellis et al. | G16H 10/60 |
| 2015/0088786 A1 | 3/2015 | Anandhakrishnan | G06N 99/00 |
| 2015/0127379 A1 | 5/2015 | Sorenson | G06F 19/00 |
| 2015/0142807 A1 | 5/2015 | Hoffman et al. | G06N 3/02 |
| 2015/0164430 A1 | 6/2015 | Hu | A61B 5/7264 |
| 2015/0302529 A1 | 10/2015 | Jagannathan | G06Q 40/08 |
| 2015/0363478 A1 | 12/2015 | Haynes | G06F 16/26 |
| 2016/0085915 A1 | 3/2016 | Seow | G06F 19/00 |
| 2016/0098387 A1 | 4/2016 | Bruno | G06F 17/27 |
| 2016/0132969 A1 | 5/2016 | Gunjan et al. | G06Q 40/08 |
| 2016/0147945 A1 | 5/2016 | MacCarthy et al. | G06F 19/00 |
| 2016/0156611 A1 | 6/2016 | Rozman | H04L 29/06 |
| 2016/0162473 A1 | 6/2016 | Cogley | G06F 40/51 |
| 2016/0371453 A1 | 12/2016 | Bowman | G06F 19/00 |
| 2016/0373456 A1 | 12/2016 | Vermeulen | G06F 16/25 |
| 2017/0076046 A1* | 3/2017 | Barnes | G16H 10/60 |
| 2017/0091162 A1 | 3/2017 | Emanuel | G06F 40/169 |
| 2017/0102693 A1 | 4/2017 | Kidd | G05B 16/41865 |
| 2017/0161372 A1 | 6/2017 | Fernandez | G06F 16/35 |
| 2017/0199928 A1 | 7/2017 | Zhao | G06F 16/24578 |
| 2017/0256173 A1 | 9/2017 | Burford | G09B 5/125 |
| 2017/0279786 A1 | 9/2017 | Peterson et al. | H04L 29/06 |
| 2017/0323485 A1 | 11/2017 | Samec et al. | G06T 19/00 |
| 2017/0337326 A1* | 11/2017 | Zhang | G16B 40/00 |
| 2017/0344646 A1 | 11/2017 | Antonopoulos | H04L 9/008 |
| 2017/0364637 A1 | 12/2017 | Kshepakaran et al. | G06F 19/00 |
| 2017/0371881 A1 | 12/2017 | Reynolds | G06F 16/248 |
| 2018/0025122 A1 | 1/2018 | Schuurkamp et al. | G06F 19/00 |
| 2018/0033279 A1 | 2/2018 | Chong et al. | G08B 21/0453 |
| 2018/0052842 A1 | 2/2018 | Hewavitharana et al. | G06F 17/3043 |
| 2018/0113986 A1 | 4/2018 | Zhu | G06F 19/3418 |
| 2018/0158146 A1 | 6/2018 | Turner | G06Q 40/02 |
| 2018/0158551 A1 | 6/2018 | Bradley et al. | G16H 40/67 |
| 2018/0164464 A1 | 6/2018 | Barnett, Jr. et al. | A61B 5/0205 |
| 2018/0173733 A1 | 6/2018 | Nath et al. | G06F 17/30 |
| 2018/0203978 A1 | 7/2018 | Basu et al. | G16H 50/30 |
| 2018/0210925 A1 | 7/2018 | Raghavan et al. | G06F 17/30 |
| 2018/0225320 A1 | 8/2018 | Saini | G06F 16/215 |
| 2018/0232443 A1 | 8/2018 | Delgo | G06Q 30/06 |
| 2018/0367557 A1 | 12/2018 | Brown | H04L 63/1425 |
| 2019/0012390 A1 | 1/2019 | Nishant | G06N 20/00 |
| 2019/0013093 A1 | 1/2019 | Slepian et al. | G16H 40/20 |
| 2019/0050445 A1 | 2/2019 | Griffith | G06K 9/6262 |
| 2019/0114511 A1 | 4/2019 | Gao et al. | G06K 9/62 |
| 2019/0156198 A1 | 5/2019 | Mars | G06N 20/20 |
| 2019/0179820 A1 | 6/2019 | El Kaed | G06F 16/2471 |
| 2019/0180757 A1 | 6/2019 | Kothari | G10L 17/005 |
| 2019/0244129 A1 | 8/2019 | Tabuchi et al. | G06F 9/5033 |
| 2019/0259108 A1 | 8/2019 | Bongartz et al. | G06Q 50/02 |
| 2019/0304582 A1 | 10/2019 | Blumenthal et al. | G16H 15/00 |
| 2019/0311299 A1 | 10/2019 | Lindner | G06F 16/248 |
| 2019/0311300 A1 | 10/2019 | Lindner | G06N 20/00 |
| 2019/0311372 A1 | 10/2019 | Lindner | G06N 20/00 |
| 2019/0318272 A1 | 10/2019 | Sassin | G06N 99/005 |
| 2019/0324964 A1 | 10/2019 | Shiran | G06N 20/00 |
| 2020/0004749 A1 | 1/2020 | Slezak | G06F 16/2462 |
| 2020/0067789 A1 | 2/2020 | Khuti et al. | H04L 41/16 |
| 2020/0074461 A1 | 3/2020 | DeRosa-Grund | G06Q 20/38 |
| 2020/0092099 A1 | 3/2020 | Austin et al. | H04L 9/14 |
| 2020/0117434 A1 | 4/2020 | Biskup et al. | G06F 8/60 |
| 2020/0160955 A1 | 5/2020 | Hansen et al. | G16H 15/00 |
| 2020/0175028 A1 | 6/2020 | Kozlowski et al. | G06F 16/252 |
| 2020/0211692 A1 | 7/2020 | Kalafut et al. | G16H 30/20 |
| 2020/0257611 A1 | 8/2020 | Hortala et al. | G06F 11/36 |
| 2020/0294642 A1 | 9/2020 | Bostic et al. | G16H 50/20 |
| 2020/0387623 A1 | 12/2020 | Bayon et al. | G06F 21/6227 |
| 2021/0090694 A1 | 3/2021 | Colley et al. | G16H 10/60 |
| 2021/0174135 A1 | 6/2021 | Liu et al. | G06K 9/62 |
| 2021/0272696 A1 | 9/2021 | DeMazumder | G16H 15/00 |
| 2021/0287656 A1 | 9/2021 | Bonafonte et al. | G10L 13/10 |
| 2021/0319796 A1 | 10/2021 | Wang et al. | G10L 15/26 |
| 2021/0374143 A1 | 12/2021 | Neill | G06F 16/24568 |
| 2021/0398024 A1 | 12/2021 | Pargunarajan et al. | G06N 20/00 |
| 2022/0004443 A1 | 1/2022 | Duggal et al. | G06F 9/54 |
| 2022/0075772 A1 | 3/2022 | Korpman et al. | G06F 16/9024 |
| 2022/0121651 A1 | 4/2022 | Korpman et al. | G06F 16/23 |
| 2022/0164337 A1 | 5/2022 | Korpman et al. | G06F 40/205 |
| 2022/0180985 A1* | 6/2022 | Connely, IV | G16H 10/60 |
| 2022/0215948 A1 | 7/2022 | Bardot | G16H 40/40 |
| 2022/0262517 A1 | 8/2022 | Van Sickle et al. | G16H 50/20 |
| 2022/0269732 A1 | 8/2022 | Pang et al. | G06F 9/3555 |
| 2022/0399112 A1 | 12/2022 | Bardot | G16H 40/40 |
| 2023/0087478 A1 | 3/2023 | Jayaram et al. | G06F 16/2365 |
| 2023/0119881 A1 | 4/2023 | Makhija et al. | G06V 30/19147 |
| 2023/0123620 A1 | 4/2023 | Simpson | G06F 3/0482 |
| 2023/0139172 A1 | 5/2023 | Booth et al. | G16H 10/60 |

(56) References Cited

U.S. PATENT DOCUMENTS

| | | | | |
|---|---|---|---|---|
| 2023/0142594 A1 | 5/2023 | Eberhardt et al. | ..... | G16H 50/20 |
| 2023/0153722 A1 | 5/2023 | Simpson | ............... | G06Q 40/04 |
| 2023/0207126 A1 | 6/2023 | Leon et al. | ........... | G06N 20/00 |
| 2023/0229999 A1 | 7/2023 | Fowles et al. | ....... | G06Q 10/063 |
| 2023/0252020 A1 | 8/2023 | Korpman et al. | .. | G06F 16/9027 |
| 2023/0252382 A1 | 8/2023 | Simpson | ............... | G06Q 50/02 |
| 2023/0260045 A1 | 8/2023 | Nawab et al. | ......... | G06V 10/82 |
| 2023/0262118 A1 | 8/2023 | Jayaram et al. | ....... | G06Q 40/06 |
| 2023/0281546 A1 | 9/2023 | Markison | .............. | G06F 18/241 |
| 2023/0325894 A1 | 10/2023 | Nilekar | .............. | G06Q 30/0601 |
| 2023/0326568 A1 | 10/2023 | Greebel et al. | ........ | G16H 50/70 |
| 2023/0326577 A1 | 10/2023 | Prince et al. | | |
| 2023/0350901 A1 | 11/2023 | Neill | ................. | G06F 16/24568 |
| 2023/0376532 A1 | 11/2023 | McCarthy et al. | ..... | G06F 16/84 |
| 2023/0409966 A1 | 12/2023 | Lindner | ................ | G06F 16/248 |

FOREIGN PATENT DOCUMENTS

| | | | | |
|---|---|---|---|---|
| CN | 110245676 | 9/2019 | .............. | G06K 9/62 |
| CN | 110998532 | 4/2020 | .............. | G06F 9/50 |
| CN | 112262368 | 1/2021 | .............. | G06F 8/30 |
| JP | 2004-318565 | 11/2004 | ............ | G06F 17/60 |
| KR | 10-1999152 | 7/2019 | ............ | G06F 17/27 |
| WO | WO 2012/023136 | 2/2012 | .............. | G01N 7/00 |
| WO | WO 2012/051389 | 4/2012 | .............. | G06F 7/00 |
| WO | WO 2017/161403 | 9/2017 | ............ | G06Q 30/02 |
| WO | WO 2018/057647 | 3/2018 | .............. | C12Q 1/68 |
| WO | WO 2018/166853 | 9/2018 | .............. | G16H 10/60 |
| WO | WO-2020150228 A1 * | 7/2020 | .............. | G06N 5/02 |
| WO | WO 2020/219971 | 10/2020 | .............. | G06N 3/04 |
| WO | WO 2021/036070 | 3/2021 | ............ | G06F 16/22 |

OTHER PUBLICATIONS

U.S. Appl. No. 18/540,583, filed Dec. 14, 2023, Lakshman et al.

International Search Report and Written Opinion issued in PCT/US2023/025897, dated Sep. 21, 2023, 10 pgs.

"Artificial Intelligence for the Data-Driven Enterprise" *Informatica*, informatica.com, 2023, 36 pages.

Gill, Navdeep Singh "Big Data Ingestion Tools and its Architecture I The Advanced Guide" Xenonstack A Stack Innovator, Apr. 29, 2023, https://www.www.xenonstack.com/blog/big-data-ingestion, 16 pages.

He et al., "The practical implementation of artificial intelligence technologies in medicine" *Nat Med*, Jan. 2019; 25(1):30-36, 15 pages.

Kaur et al., "AI based HealthCare Platform for Real Time, Predictive and Prescriptive Analytics using Reactive Programming" *Journal of Physics: Conference Series* 933 (2018), 13 pages.

Krugman, Brandon, "Converting Medical Service Provider Data into a Unified Format for Processing" (2015).*Master's Theses* (2009-). Paper 322. http://epublications.marquette.edu/theses_open/322, 50 pages.

U.S. Appl. No. 17/960,565, filed Oct. 5, 2022, Kittel.

U.S. Appl. No. 17/988,505, filed Nov. 16, 2022, Gupta et al.

U.S. Appl. No. 17/991,554, filed Nov. 21, 2022, Kumar et al.

U.S. Appl. No. 18/143,397, filed May 4, 2023, Gupta et al.

U.S. Appl. No. 18/420,434, filed Jan. 23, 2024, Raghuvansh et al.

Office Action issued in U.S. Appl. No. 17/960,565, dated Aug. 22, 2024, 17 pgs.

Notice of Allowance issued in U.S. Appl. No. 17/991,554, dated Sep. 26, 2024, 9 pgs.

EPO Supplementary Search Report issued in EP20754922.1, dated Oct. 4, 2022, 12 pgs.

International Search Report and Written Opinion issued in PCT/US2020/13802 dated Mar. 25, 2020 (10 pgs).

International Search Report and Written Opinion issued in PCT/US2020/16827 dated Apr. 22, 2020 (7 pgs).

International Search Report and Written Opinion issued in PCT/US2022/045784, dated Feb. 8, 2023, 10 pgs.

International Search Report and Written Opinion issued in PCT/US2022/050117 dated Mar. 3, 2023 (8 pgs).

International Preliminary Report on Patentability issued in PCT/US2020/013802, dated Aug. 10, 2021, 7 pgs.

International Preliminary Report on Patentability issued in PCT/US2020/016827, dated Aug. 10, 2021, 5 pgs.

International Search Report and Written Opinion issued in PCT/US2022/050616 dated Mar. 27, 2023 (7 pgs).

International Search Report and Written Opinion issued in PCT/US2023/021014, dated Jul. 28, 2023, 9 pgs.

Notice of Allowance issued in U.S. Appl. No. 16/387,016, dated Feb. 10, 2020 (14 pgs).

Notice of Allowance issued in U.S. Appl. No. 16/363,897, dated Jul. 30, 2020 (18 pgs).

Notice of Allowance issued in application No. 16/743, 175, dated Jul. 31, 2020 (18 pgs).

Office Action issued in U.S. Appl. No. 16/387,016, dated Jun. 25, 2019 (11 pgs).

Office Action issued in U.S. Appl. No. 16/387,016, dated Oct. 17, 2019 (17 pgs).

Office Action issued in U.S. Appl. No. 16/363,897, dated Sep. 9, 2019 (38 pgs).

Office Action issued in U.S. Appl. No. 16/363,897, dated Feb. 26, 2020 (36 pgs).

Office Action issued in U.S. Appl. No. 16/743,175 dated Mar. 23, 2020 (21 pgs).

Office Action issued in India Application No., 201921043365, dated Dec. 10, 2021, 7 pgs.

Arjona et al. "Triggerflow: Trigger-based orchestration of serverless workflows", Future Generation. Computer Systems 124, 2021, pp. 215-229.

Carver et al. "In Search of a Fast and Efficient Serverless DAG Engine", George Mason University, Nov. 18, 2019, 10 pgs.

Datavant—Connecting the world's health data, slide presentation, https://www.healthra.org/wp-content/uploads/2018/10/Datavant-Overivew-Deck_Prepared-for-HRA_v20181002-1.pdf Oct. 2018, 15 pgs.

"De-identification and re-identification of PII in large-scale datasets using Cloud DLP", Cloud Architecture Center, https://cloud.google.com/architecture/de-identification-re-identification-pii-using-cloud-dlp, Aug. 11, 2022, 9 pgs.

Morid et al. "Supervised Learning Methods for Predicting Healthcare Costs: Systematic Literature Review and Empirical Evaluation", 2018, AMIA Annu Symp Proc. pp. 1312-1321.

Shin, "Encoding Database Schemas with Relation-Aware Self-Attention for Text-to-SQL Parsers", arXiv: 1906.11790v1 [cs.LG] Jun. 27, 2019, 10 pgs.

Suleiman et al., "Deep Learning Based Abstractive Text Summarization: Approaches, Datasets, Evaluation Measures, and Challenges", Hindawi, Mathematical Problems in Engineering, vol. 2020, Article ID 9365340, Aug. 24, 2020, 29 pgs.

Wang et al. "Detecting Transportation Modes Based on LightBGM Classifier from GPS Trajectory Data", 2018 26th International Conference on Geoinformatics, Kunming, 2018, pp. 1-7.

Zhang et al. "Health reform and out-of-pocket payments: lessens from China", Health Policy and Planning, vol. 29, Issue 2, Mar. 2014, pp. 217-226, https://doi.org/10.1093/heapol/czt006.

Iyengar et al. "A Trusted Healthcare Data Analytics Cloud Platform", 2018 IEEE 38th International Conference on Distributed Computing Systems (ICDCS), Vienna, 2018, pp. 1238-1249.

Chen et al., "Learning Semantic Annotations for Tabular Data", Proceedings of the Twenty-Eighth International Joint Conference on Artificial Intelligence (IJCAI-19), Aug. 2019, 7 pgs.

Gorman et al., "Structured Abbreviation Expansion in Context", arXiv:2110.01140v1 [cs. CL] Oct. 2021, 11 pgs.

Ratinov et al., "Abbreviation Expansion in Schema Matching and Web Integration", Proceedings of the IEEE/WIC/ACM International Conference on Web Intelligence (WI'04), 2004, 5 pgs.

Xu et al., "Modeling Tabular Data using Conditional GAN", 33rd Conference on Neural Information Processing Systems (NeurIPS 2019), Vancouver, Canada, 11 pgs.

* cited by examiner

300

Search for a Patient:

First Name: Joy

Last Name: Lawson

Date of Birth: 05/13/1955

Search

Device #1 or Application #1

---

Patient: Joy Lawson
DOB: 05/13/1955

Overview

PCP: Sarah West (9375378374)
Last Encounter: 09/23/2020
Last Annual Wellness Visit: 04/16/2020
ED Visits in last year: 3 ED (last visit on 05/17/2020)
IP Visits in last year: 2 IP (last visit on 11/02/2020)

Device #1 or Application #1

---

Patient: Joy Lawson
DOB: 05/13/1955

Vitals

Height: 172.7 cm
Weight: 163 lbs.
BMI: 54.7
Blood Glucose: 140 mg/dL
Blood Pressure: 130/80

Device #2 or Application #2

---

Patient: Joy Lawson
DOB: 05/13/1955

Medications

Acetaminophen: 650mg orally every 6 hours
Atenolol: 50mg orally once daily
Aspirin: 80mg orally once daily
Metformin: 500mg orally once daily
Folic Acid: 1mg orally once daily Device #3 or Application #3

---

Patient: Joy Lawson
DOB: 05/13/1955

Allergies

Penicillins: Very mild
Codeine: Very mild
Bee venom: Moderate

Device #4 or Application #4

---

Patient: Joy Lawson
DOB: 05/13/1955

Lab Results

Microalbumin: 13 mg/Gm (Normal)
Est. average glucose: 153 mg/dL (High)
Hgb A1c MFr  Bid: 5.4% (Normal)
Tobacco Use: Yes Device #5 or Application #5

FIG. 4

SYSTEM AND METHOD FOR AUTOMATIC DISPLAY OF CONTEXTUALLY RELATED DATA ON MULTIPLE DEVICES

CROSS REFERENCE TO RELATED APPLICATION

This application claims benefit of U.S. Provisional Application Ser. No. 63/354,164 filed Jun. 21, 2022, the entire disclosure of which is incorporated herein by reference.

TECHNICAL FIELD

The present subject matter, in general, relates to automatic display of contextually related data in multiple devices simultaneously and in particular, relates to a method and system for automatic visual display of data on one or more secondary devices, said data being contextually related to data displayed on a primary device.

BACKGROUND

In today's healthcare environment, electronic medical records are increasingly utilized in various healthcare institutions, such as clinics and hospitals, as the primary source of clinical information. Electronic medical records provide an accurate and up to date information of patients such as patient diagnosis, previous treatments, healthcare reports, medical histories, and so on, which are quite helpful in providing an optimum healthcare treatment to patients.

With evolution of distributed departments depending upon different specialties in the hospitals, there has been an increased demand of sharing patient information among departments. Additionally, in some cases, it is desirable to share medical data of patients with other medical institutions. This can be done by sharing patient record among multiple electronic devices. For example, the hospital facilities typically include a user interface screen for displaying relevant data of patients. In some other alternative instances, sharing of patients data from one device to another is accomplished by pushing such data from the first device to the other. Real time sharing of information is also known in the art.

Traditionally, sharing of patient information is generally performed by streaming the relevant data between different devices. Such data sharing can often be delayed or become cumbersome due to the large amount of patient data, and/or the connection limitations of current streaming technologies. Moreover, such streaming/screen sharing solutions possess additional shortcomings such as, not allowing multiple devices to be aggregated onto a single device. Also, streaming systems that permit remote viewing of a user interface also often do not permit the user interfaces from multiple devices to be aggregated on a single screen. Further, the existing systems do not allow display of information from one device, other than the information corresponding to the device, which is simultaneously displayed on a monitoring device. For example, it may be desired that an X-ray report of a patient is to be shared with a secondary device, wherein only some of the patient's information is accessed onto the primary device. However, this is not feasible by using current streaming solutions. Additionally, such streaming/screen sharing solutions do not provide adequate protection for confidential or personal data from being shared while sharing the patient's information.

Accordingly, there have been significant efforts towards developing of various automated systems that allow sharing various patient information, such as Electronic Health Record (EHR); Electronic Medical Record (EMR); Personal Health Record (PHR) and/or a sub-portion thereof, between multiple devices, generally belonging to different healthcare stakeholders. Additionally, such systems are focused on ensuring privacy such that a primary user or an owner of the information, is able to control who is allowed to access their medical data.

U.S. Pat. No. 9,633,404 discloses a method for co-browsing of patient records on multiple communication devices. The method includes setting up a communication session between a first communication device and one or more second communication devices, where the communication session is initiated by the first communication device. Further, the method includes accessing one or more patient records via a server, where one or more patient records are accessed at the first communication device. While such a solution allows the second communication device to access the information from a data server, it still requires setting up a connection between two devices.

U.S. Publication. Number 2017/0364637A1 discloses a method of sharing health record of a patient with his family members onto computing devices. The reference utilizes API with predetermined permissions for the computing devices so as to allow sharing therewith. Further, the health record is shared via the backend system once the permission is displayed. This document, however, still requires the patient to manually allow selective permission for allowing the data to be downloaded. Moreover, it does not automatically display details of the patient whose record is being viewed on the primary device.

Some other known solutions provide for a specific application that needs to be installed on each device such that each application is connected to and is able to access a patient health record database. In such cases, when the patient detail is shared between devices, the application can search and take out relevant information directly from the database. However, such a solution is also not automatic and is not implemented truly in a real time.

Thus, a heretofore unaddressed need exists in the industry to address the aforementioned deficiencies and inadequacies.

SUMMARY

In one aspect of the present disclosure, a system for automatic display of contextually related information, such as patient healthcare data, between a plurality of communication devices in a real time, is disclosed. The system comprises a first communication device, connected to one or more first data sources, comprising a plurality of contextual information of a predetermined information type, stored therein. The first communication device includes a first application provided with a first application interface. The first application interface is communicatively connected to a backend server.

The system further includes one or more second communication devices, each second communication device comprising a secondary application having a second interface, installed thereon. The one or more secondary devices are also connected to one or more second data sources, also comprising a plurality contextual information stored therein. The secondary application is further connected to the backend server and is adapted to receive one or more data streams, related to at least one or more contextual information, from the backend server. Preferably, the contextual information includes patient identification data from patient healthcare information, including but not limited to, an EMR, PHR and the like.

In operation, the first application interface is configured to detect an access of a patient healthcare information, such as an EMR, to the first computing device. Thereafter, the first application interface determines the context data by capturing and/or recognizing the accessed patient healthcare information. The context data thus determined is sent to the backend server in real time, which in turn creates a data stream corresponding to the context data. The context data on thus received onto the one or more second communication devices in real time is used by the one or more second application interface to visualize the patient healthcare information onto second computing unit.

In an embodiment, the plurality of first data sources and the second data sources comprises data-sets related to a plurality of patients' healthcare data such as EMR, PHR, specific medical records such as lab tests, previous diagnosis reports, treatment history, patient illness, patient information such as name, address, telephone number, and so on.

In an embodiment, each of the first application as well as the plurality of secondary applications is authorized by a primary user allowing the secondary applications to receive data stream in real time from the information accessed onto the primary device.

In an embodiment, the communication device comprises a computing device selected from one or more of but not limited to a smartphone, tablet, workstation, and the like, In another aspect of the present subject matter, a method for automatic display of contextually related information, such as patient healthcare data, between a plurality of communication devices in a real time, is disclosed. The method includes determining one or more context data related to at least one of the contextual information on a first application interface installed within a first communication device. Particularly, the one or more context data is determined by detecting and/or capturing and/or recognizing, an access of the one or more contextual information onto the first communication device. The method further includes communicating the one or more context data from the first application interface to a backend server in real time. Thereafter, the method includes creating a data stream on the basis of the one or more contextual information received from the first application interface. The method furthermore includes receiving a real-time data stream related to the at least one designated patient at one or more subscribed second application interface installed within one or more second communication devices.

The contextual information includes patient information and/or healthcare data including one or more of but not limited to EMR, PHR, specific medical records such as lab tests, previous diagnosis reports, treatment history, patient illness, and so on.

The context data comprises the data information determined by the accessed contextual information such as a patient identification data and is selected from one or more of but not limited to a Patient ID, Patient Name, Date of Birth, Patient Location, SSN, mobile number and other context that may help in determining the patient's healthcare information.

In an embodiment, the data stream comprises a combination of the context data either completely and/or at least partially, and/or any additional data related to the context data received from the first communication device.

In an embodiment, the access of one or more patient healthcare information is detected by a detection module configured to communicate with one or more processes of the operating system to determine an access of one or more type of applications on the first communication device.

In an embodiment, capturing of access of one or more patient healthcare data includes capturing a screenshot of a GUI of the program where the healthcare data is accessed.

In an embodiment, the recognition of the captured access of one or more patient healthcare data includes recognizing the information from the image by using any predetermined mechanism including but not limited to OCR, Image Matching and/or any other suitable application.

In yet another aspect of the present disclosure, a computer program tangibly embodied on a non-transitory computer-readable storage medium for accessing patient healthcare data between a plurality of communication device in a real time, using contexts thereof, is disclosed. The non-transitory computer readable storage medium includes one or more instructions that, when executed by one or more processors, cause the one or more processors to determine one or more context data related to at least one of a contextual information, on a first application interface installed within a first communication device. Particularly, the one or more context data is determined by detecting and/or capturing and/or recognizing, an access of the contextual information onto the first communication device. The programming instruction further causes a communication of the one or more context data from the first application interface to a backend server. Thereafter, the programming instruction causes creation of a data stream on the basis of the one or more contextual information received from the first application interface. The programming instructions further allow receiving a data stream related to at least one designated patient at one or more subscribed second application interface installed within one or more second communication devices.

The details of one or more implementations are set forth in the accompanying drawings and the description below. Other aspects, features and advantages of the subject matter disclosed herein will be apparent from the description, the drawings, and the claims.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

FIG. 4 illustrates exemplary additional contextual information in accordance with different embodiments of the present subject matter.

DETAILED DESCRIPTION

Figure 1:
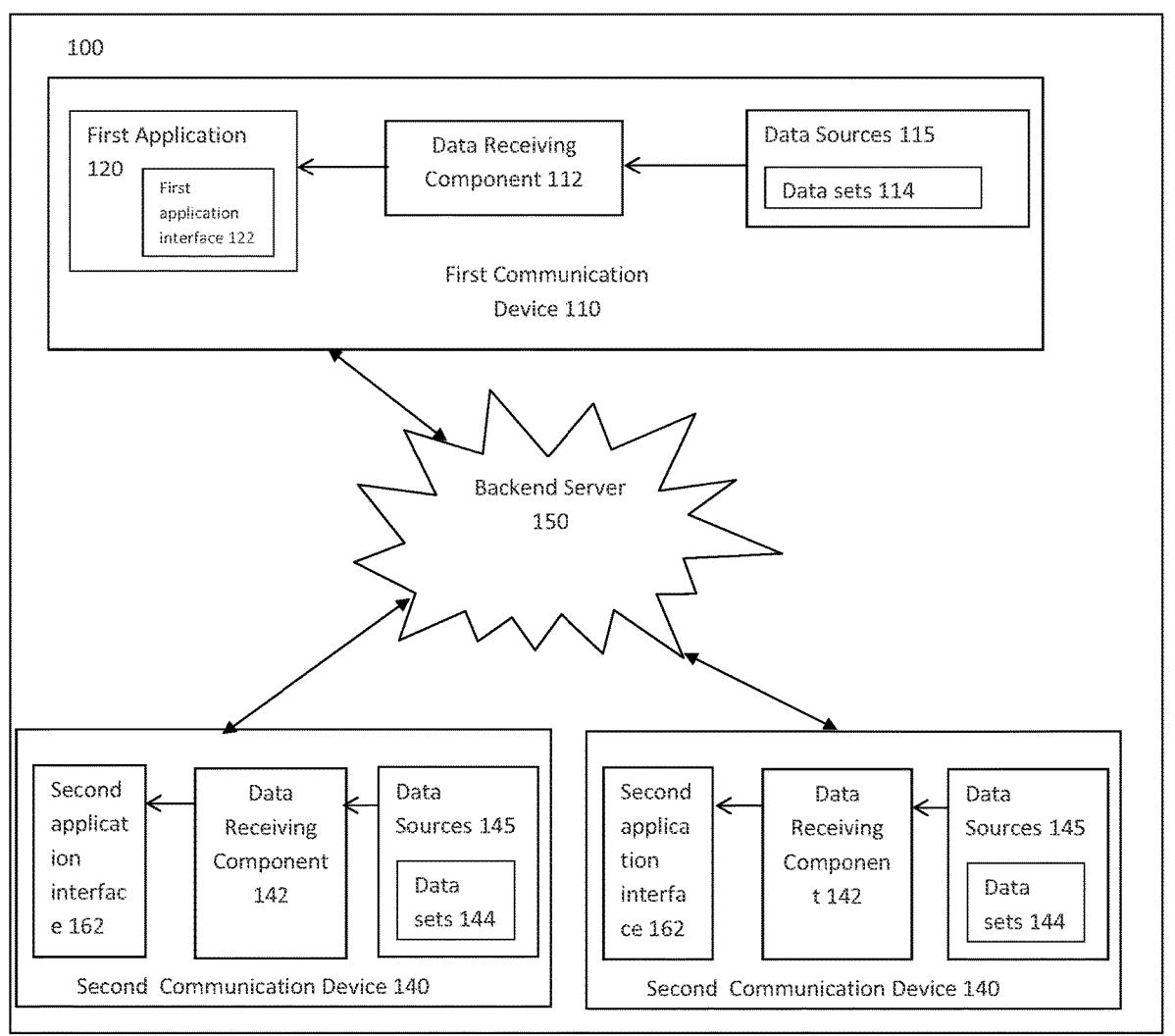
FIG. 1 illustrates a block diagram of a system for automatic display of contextually related information between a plurality of communication devices in a real time in accordance with an embodiment of the present subject matter.

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented, and the needs of a particular application may yield multiple alternate and suitable approaches to implement the functionality of any detail described herein. Therefore, any approach may extend beyond the particular implementation choices in the following embodiments described and shown.

Embodiments of the invention are directed to methods, computerized systems, and computer-readable media for use in enabling an access of context based healthcare data on multiple communication devices that may be utilized by a variety of healthcare applications. In a preferred embodiment, the present application discloses a system and method for sharing patient's context data between a plurality of communication device in real time. Particularly, the system shares data on the basis of one or more context determined about a patient information accessed onto a primary device. Thereafter, on the basis of one or more context, sharing and visualizing a data stream onto a secondary device onto an application interface installed thereon. The system is further adapted to automatically send push notifications such that the data streams can be visualized in a real time as soon as the context is determined onto the primary device. The application interface is generally provided in the form of a GUI application that could be installed on a communication device. The application interface may be in the form of a mobile application. However, in other embodiments, the system may be in form of a web-based automated service accessible on a generally known computing unit.

In an embodiment, the system of present subject matter is adapted to identify a relevant data stream from a designated patient's health record including but not limited to EMR, EHR, specific information that describes various aspects of the patient state, including patient vitals, lab results, medication orders, diagnosis codes, condition codes, clinical orders, indexed values from clinical notes or other text documents, patient demographic information, patient history, patient images, and a variety of other patient information, which may be utilized for the purpose of determining any underlying patient information for optimizing the diagnosis and/or treatment. Further, the record may also be utilized in combination with another utility onto the communication device for various purposes such as for example, contacting/calling the patient, any other healthcare stakeholder related to the patient treatment, and the like. It is to be understood that unless otherwise indicated, this invention need not be limited to applications for healthcare facility. As a person of ordinary skill in the art would appreciate, variations of the invention may be applied to other possible context-based data sharing applications in any other field of daily life such as for example within financial services such as a banking industry, investment industry, stock trading, mortgage industry, various services and products where context-based data sharing in real time, is required. Moreover, it should be understood that embodiments of the present invention may be applied in combination with various other management systems such as facility management systems, human resource management system, occupational management systems, clinical systems, and the like, for various other possible applications.

It must also be noted that, as used in this specification and the appended claims, the singular forms "a," "an" and "the" include plural referents unless the context clearly dictates otherwise. Thus, for example, the term "a data-source" is intended to mean a single data-source or a combination of data-sources, "an API" is intended to mean one or more API for a same purpose, or a combination of API for performing different program executions.

References to "one embodiment," "an embodiment," "at least one embodiment," "one example," "an example," "for example," and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

FIG. 1 illustrates a block diagram of a system for automatic display of contextually related information between a plurality of communication devices in a real time in accordance with an embodiment of the present subject matter. The system 100 includes a first communication device 110 having one or more data-receiving components 112 adapted to receive one or more datasets 114 from one or more first data sources 115. The first data sources 115 include a plurality of datasets pertaining to data received from a plurality of data sources, such as electronic medical records crawlers, clinical and administrative data collectors, claims data collectors, document feed collectors, and medical device feed collectors, and other data sources that collect patient healthcare data from patients or providers, documents, and medical devices. The data sets 114 generally include various data of designated patient's health record, such as EMR, EHR, specific information that describes various aspects of the patient state, including patient vitals, lab results, medication orders, diagnosis codes, condition codes, clinical orders, indexed values from clinical notes or other text documents, patient demographic information, patient history, patient images, and a variety of other patient information, which may be utilized for the purpose of determining any underlying patient information and/or for optimizing the diagnosis and/or treatment.

The system 100 further includes a first application 120 associated with a backend server 150 and adapted to communicate therewith. In some embodiments, the first application 120 may at least partially reside on the first communication device 110 and facilitates a communication with the backend server 150. In some instances, the first application 120 may be downloaded from the backend server 150 and/or any other possible sources and installed onto the first communication device 110. Further, in such instances, the first application 120 may be in form of different versions selectable in accordance with the type of communication device. For example, a smartphone application is further divided into an android and/or an iOS application, a software application downloadable on laptop/computers, and the like. Any and all such variations are contemplated to be within the scope of embodiments of the present invention.

In other embodiments, the first application 120 may be in the form of a web based automated service that may communicate via a Web-based communication, using, for example, a Web browser to communicate with the backend server 150 via the Internet. Any and all such variations are contemplated to be within the scope of embodiments of the present invention.

Figure 2:
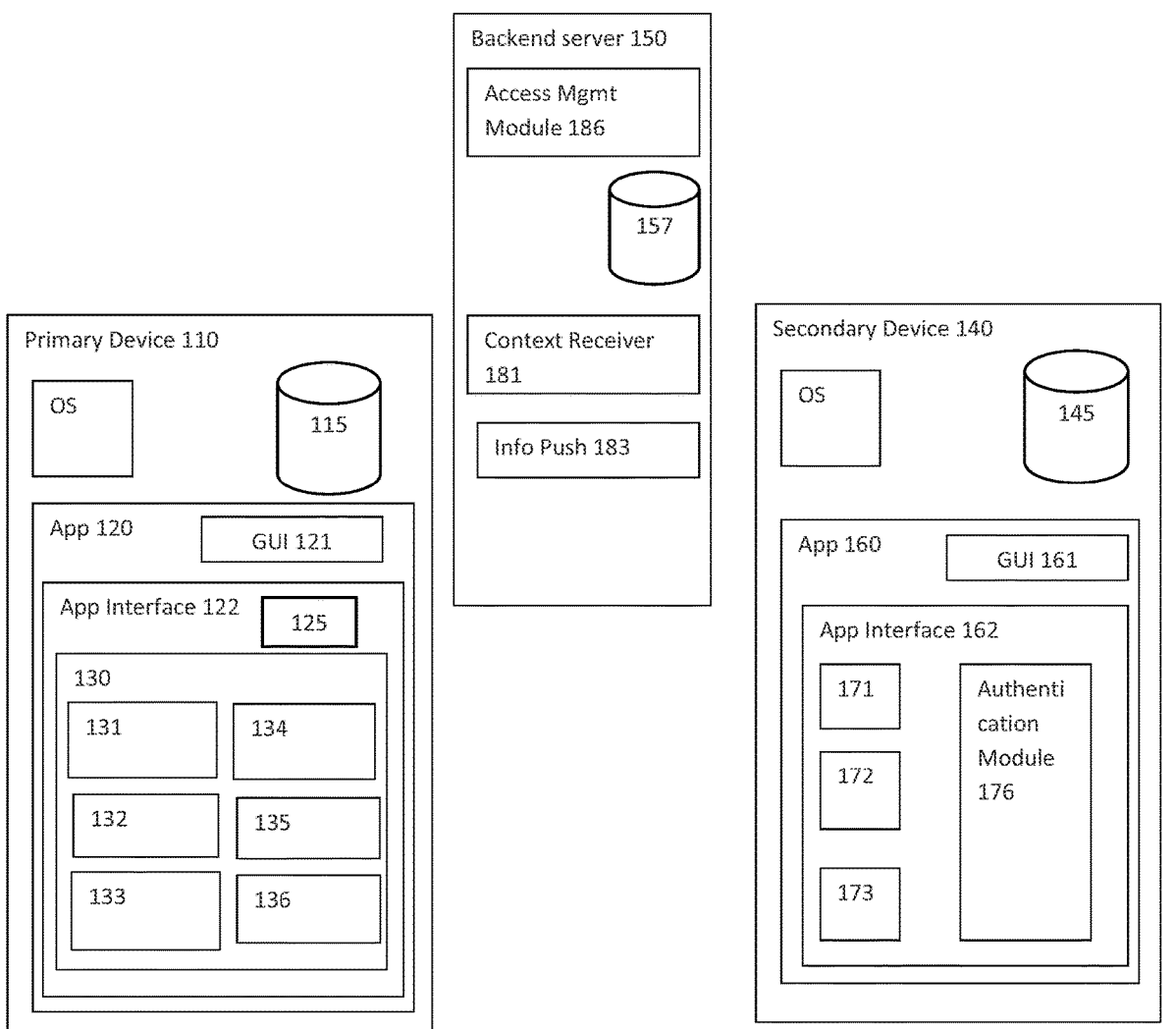
FIG. 2 is a system block diagram illustrating an exemplary client server architecture device, in accordance with the preferred embodiment of the present subject matter.

With respect to FIGS. 1 and 2, the first application 120 includes a first graphical user interface 121 for visualizing one or more visual interfaces thereon, and a first application interface 122 generally adapted to determine one or more context data 125 related to one or more patient healthcare data sets 114, when accessed onto the first communication device 110.

The first graphical user interface 121 is a module adapted to manage one or more user interactions with the application 120 via one or more components of the first communication device 110. In some embodiments, the GUI 121 comprises a webpage accessible over the Internet. In another embodiment, the GUI 121 is provided via an application or service (including an Operating System service) on the first communication device 110 and may also be controlled in association with one or more parts of the first application 121. The one or more interactions may include but are not limited to prompting a primary user (not shown) of the first application 120 to input the authentication information, display one or more data streams related to one or more designated patients, view context data determination history of the application 120, and any other visualization. In some embodiments, the GUI may be adapted to provide one or more functionality and/or features including but not limited to interface elements (such as graphics buttons, sliders, menus, audio prompts, alerts, alarms, vibrations, pop-up windows, notification-bar or status-bar items, in-app notifications, or other similar features for interfacing with a user), queries, and prompts.

The first application interface 122 includes one or more executable sub-applications 130. In an embodiment, the executable sub-applications 130 includes a detection sub-application 131, a capturing sub-application 132, are recognition sub-application 133, a context determination sub-application 134, a backend sharing sub-application 135, an authentication module 136. In a preferred embodiment, each executable sub-application 130, includes one or more programming instructions that cause a processor of the first communication device 110, utilize one or more resources and/or sub-components and/or sub-programs of the computing device 110, perform one or more predetermined activities and/or process steps (as disclosed in FIGS. 5 & 6), as required by the application interface 122. Such predetermined activities and/or process steps may be performed automatically in response to executable instructions from the corresponding executable sub-applications 130 without user direct initiation of the activity. However, in some other embodiments/instances, such predetermined activities and/or process steps may be performed, wholly or partially in response to the primary user's command and/or input.

The detection executable sub-application 131 is a module adapted to identify and/or detect an access of one or more contextual information onto the first communication device 110. In a preferred embodiment, the detection executable sub-application is 131 generally configured to call one or more operating system processes and/or any other services operating on the first communication device 110, which in turn determines access of one or more predetermined application/services on the first communication device 110. The predetermined applications are generally the applications, which are used to open and/or access and/or process the contextual information on the first communication device 110. For example, in some instances the predetermined application may be selected from one or more of but not limited to a web browser, Patient EMR File Extensions supporting programs. In some other embodiments, the detection of access of the contextual information may be done by using external API configured to determine such an access. In yet other embodiments, any conventional yet suitable known mechanism for detecting an access of a predetermined kind of information may be used without deviating from the scope of the current disclosure.

The context capturing executable sub-application 132 is a module adapted to capture a screenshot of the application and/or the contextual information when accessed onto the first communication device 110. The context capturing sub-application may include and/or collaborate with one or more screen capture tools, such as including, but not limited to optical character recognition, using pixel comparison and matching, feature extraction, image recognition using deep learning models, machine learning techniques, or other computer vision techniques or algorithmic processing or other methods. In some embodiments, the context capturing sub-application may be configured to determine and/or intercept a context data, such as user and patient context, Date of context, and the like. In such embodiments, the screen capture tool is particularly focused at taking a screenshot of the region displaying the context data thereat. In preferred embodiments, the screen capturing tool shall mean any hardware, software, computer readable medium, computer program, or integrated circuit configured to store in a memory at least portions of screen shots of an output presented on the display screen by an access application, when the application is running and to also later present the stored screenshots of output on the display screen when the application is not operating, is not powered or is otherwise not running. For the purpose of this disclosure, a "screenshot", also known as a screen capture or screen dump, is an image taken or captured by screen capture tool to record the visible items displayed on display screen. In one embodiment, the screenshot may comprise the entire and/or one or more portions of the screen in a bitmap image format such as bitmap (BMP), device independent bitmap (DIB), portable network graphics (PNG) or Joint Photograph Experts Group (PEG). In other preferred embodiments, the screen capture sub-application is configured to automatically capture a screen shot of one or more portion of the screen after a regular predetermined time interval and over an extended period of time. In some other embodiments, the screen may be captured for a period of time in form of video.

The recognition sub-application 133 is a module adapted to recognize text and/or information from one or more screenshot captured by the capture executable sub-application 132. In preferred embodiments, the image recognition module may include any hardware, software, computer readable medium, computer program, or integrated circuit configured to recognize text and/or object from at least a portion of screen shots stored within a memory and/or displayed on a screen. The recognition sub-application may include one or more text detection applications such as an Optical Character Recognition (OCR), video detection, image recognition, object recognition, motion estimation, and the like, selected from one or more of but not limited to an OTSU's Algorithm, K-Nearest Neighbor's Algorithm, Adaptive Recognition Algorithms. Further, in some embodiments, the recognition sub-applications may be used in combination with machine learning/Artificial Intelligence algorithms, such as heuristic models, neural networks, fuzzy logic models, expert system models, and the like, to increase the data-set and/or in turn improve the accuracy of the text/information recognition many folds. In other embodiments, any known suitable algorithms and/or mechanisms may be utilized for the purpose of recognizing/interpreting text from the captured screenshot.

The context determination sub-application 134 is a module adapted to determine one or more context data from a dataset of text/objects recognized by the recognition sub-application 133. The context determination sub-application 134 may include one or more context determination models, such as in the form of user defined and/or machine learning/ fuzzy logics/deep learning model and/or other static/dynamic models, which may further include and/or train various context recognition libraries to determine relevant context data from a data set of plurality of words/terms/texts and/or objects. Particularly, the context data may be identified/stored in the memory of the first communication device along with one or more additional details such as a data/time stamp, which may be utilized to assure that the context sharing is performed in real time when shared onto the secondary communication devices 140. The context data may be defined according to a schema, which specifies the information to be transferred across the communication devices, operating systems, applications, or locations for sharing context, and may correspond to a particular task or category of task, experience, or content, or a type of application, service, or device. For example, the context data schema generally is utilized to define one or more identifiers that may be used to reproduce and/or search additional information related to the contextual information accessed onto the first communication device 110, and relevant to the second communication devices 140. For example, when the contextual information includes Patient Healthcare record and/or information, such as various data of the designated patient's health record including but not limited to EMR, EHR, specific information that describes various aspects of the patient state, including patient vitals, lab results, medication orders, diagnosis codes, condition codes, clinical orders, indexed values from clinical notes or other text documents, patient demographic information, patient history, patient images, and a variety of other patient information, which may be utilized for the purpose of determining any underlying patient information and/or for optimizing the diagnosis and/or treatment. In such instances, an example of context data includes but is not limited to patient identifier (ID information) including characters or codes for identifying a patient, such as a patient name, a patient ID, a barcode, date of birth and/or other relevant information about the patient, which can be used to find other information about the patient. Accordingly, the context data may be determined for other type of contextual information including but not limited to financial records, bank account details, stock market trading, product data, and the like without limiting to any specific industry and/or application thereof.

The context sharing sub-application 134 is a module adapted to share the context data determined at the first application 120 for the primary user with the backend server 150. The context sharing sub-application 134 may use one or more communication means connecting the first application

120 with the backend server 150. In other embodiments, the communication channel may include one or more REST (Representational State Transfer) API adapted to automatically request and retrieve data from the memory of the first communication device 110 and share with the backend server 150. In yet other embodiments, any known suitable means/methods of sharing information between an application and a backend server may be utilized.

The authentication module 136 may be adapted to identify and/or authenticate a primary user uniquely associated with the first communication device 110. Particularly in some embodiments, the authentication module 136 may be associated to a corresponding module onto the backend server 150 so as to authorize the primary user an access onto the first application 120 of the first communication device 110. The authentication module 136 is generally adapted to be executed in collaboration with the user interface 121 so as to enable the primary user to communicate therethrough. In a preferred embodiment, the graphical user interface 121 comprises an authenticating form (not shown) adapted to receive one or more inputs from the primary user. Such an authenticating form may require the primary user to fill authentication information therein. The authentication information may be, in accordance with one or more authentication methods, selected from but not limited to a combination of login ID/email ID/user ID/device ID and a password; one or more biometric measurement (including fingerprints, facial and/or eye feature matching); and/or a pattern to be designed onto the first communication device and/or security questions; one-time password (OTP) tokens (e.g., as generated in conjunction with an email/phone number of the registered user; and/or any conventionally known authenticating/identifying mechanism known in the art and any possible combinations thereof.

The authentication module 136 further includes a control mechanism adapted to set one or more user profiles, authentication methods/login identifiers to enable access parameters, privileges, level of permissions, device type/identifier, and the like for enabling the primary user to access the first application 120. However, in an embodiment, access may be provided automatically by authenticating the first communication device 110 without a need of the primary user providing an input for the authentication.

In an embodiment, the authentication module 136 sends over the authentication information to the backend server 150, which in turn validates/disallows the identification/ authorization and automatically retrieves device information/user profile/settings, and the like, corresponding to the primary user.

In some embodiments, the process of authentication may be used to provide consent of the primary user to allow various sub-applications 130 of the first application 120, to be executed as required, such that the transfer of one or more context data from the first communication device 110 to the backend server 150 is authorized by the primary user. However, in some instances, such a permission is received from the primary user during installation of the first application 120 onto the first communication device 110 and is therefore, not required to include such consent each time the user logs in to the first application 120.

In an embodiment, the control mechanism of the authentication module 136 may be used to configure the transfer to be performed. For example, in some preferred instances, the context data is determined by the first application 120 and sent over to the backend server 150. However, in some other instances, the first application 120 just detects and captures an access of the contextual information and sends over the screenshot to the backend server 150. In all such instances, the backend server 150 may include additional sub-modules to determine context from the captured access screenshot received from the first application 120. Further, in some embodiments, the primary user may provide authorization that enables a sharing the context of only a predetermined information type. However, in other embodiments, the sharing is not limited to any information type. In some instances, the authorization module 136 may be used to enable a sharing of context from a predetermined location, connections, and the like.

In an embodiment, it is to be contemplated that the first application 120, in addition to the disclosed executable sub-applications 130 may also include one or more computer programs, software services, or routines, adapted to operate on the first communication device 110. Further, such programs/services/routines may be able to work in a stand-alone manner and/or may further be supported by other programs/applications that run on the first communication device 110 and are supported by operating system thereof.

It is to be further contemplated that the application interfaces including the first application interface 122 and the second application interface 162, may be in the form of a sub-module of the corresponding applications 120, 160, respectively. However, in other embodiment, the first application interface 122 and the second application interface 162 may be distinct and/or operationally separate from the corresponding applications 120, 160 and may be provided in any suitable form known in the art such as for example, back-end agents, separate applications, or any other installable and/or web based module adapted to perform the functions as specified in relation to the corresponding communication devices 110, 140.

The system 100 further includes one or more second communication devices 140, similar to the first communication device 110, having one or more data-receiving components 142 adapted to receive one or more data-sets 144 from one or more first data sources 145. The second communication device 140 includes a secondary application 160, also associated with a backend server 150 and adapted to communicate therewith. In some embodiments, the second application 160 may at least partially reside on the second communication device 140 and facilitates a communication with the backend server 150. In some instances, the second application 160 may be downloaded from the back-end server 150 and/or any other possible sources and is installed onto the second communication device 140. Further, in such instances, the second application 160 may be in form of different versions selectable in accordance with the type of communication device. For example, a smartphone application further divided into an android and/or an iOS application, a software application downloadable on laptop/ computers, and the like. Any and all such variations are contemplated to be within the scope of embodiments of the present invention.

In other embodiments, the second application 160 may be in form of a web-based automated service that may communicate via a web-based communication, using, for example, a Web browser to communicate with the backend server 150 via the Internet. Any and all such variations are contemplated to be within the scope of embodiments of the present invention.

In an embodiment, the second application 160 includes a second graphical user interface 161, for visualizing one or more visual interfaces thereon, and a second application interface 162 generally adapted to receive one or more data streams 165 related to one or more patient healthcare data sets 114 when accessed onto the first communication device 110.

The second graphical user interface 161 is a module adapted to manage one or more user interactions with the application 160 via one or more components of the second communication device 140. In some embodiments, the GUI 161 comprises a webpage accessible over the Internet. In another embodiment, the GUI 161 is provided via an application or service (including an Operating System service) on the second communication device 140 and may also be controlled in association with one or more part of the second application 160. The one or more interaction may include but is not limited to prompting a secondary user (not shown) for the purpose of authorization, display one or more data streams 165 related to one or more designated patients, viewing data stream history of the one or more secondary applications 160, managing an access to the context data (e.g., setting or modifying access parameters), and any other visualization to be viewable by the secondary user. In some embodiments, the GUI 161 may be adapted to provide one or more functionality and/or features such as including but not limited to interface elements (such as graphics buttons, sliders, menus, audio prompts, alerts, alarms, vibrations, pop-up windows, notification-bar or status-bar items, in-app notifications, or other similar features for interfacing with a user), queries, and prompts.

The second application interface 162 includes one or more executable sub-applications 170. In an embodiment, a data-stream receiving/notification sub-application 171, a contextual information searching sub-application 172, an information visualization sub-application 173, and a second authentication module sub-application 176. However, it is to be contemplated that one or more other sub-application as desired, and necessary to provide any of the afore-mentioned features/functionalities may also be present without deviating from the scope of the current disclosure. As can be understood from the name, the data-stream receiving sub-application 171 is a module that is adapted to allow receiving of one or more data streams from the backend server 150 onto the second communication device 140. In some embodiments, the sub-application 171 may further be adapted to generate one or more notification/prompts when a data-stream is received thereat.

The contextual information searching sub-application 172 is a module adapted to automatically search the one or more second data sources 145, for additional contextual information related to the contexts received from the backend server 150. The additional contextual information is searched in accordance with a user role/schema/profile of the secondary user. For example, when a context received is a patient ID from a patient health record, at the secondary device 140 of a laboratory, the additional data that is searched for, may be various lab reports, sample details, and the like relevant to the user profile i.e., laboratory. The information visualization sub-application 173 is a module adapted to automatically overlay a visualization of the additional contextual information received and/or determined onto the graphical user interface 161 of the second communication device 140. In some embodiments, the graphical user interface 161 includes a predetermined interface region for allowing a display of such additional contextual information thereat.

The second authentication module 176 may be adapted to identify and/or authenticate a secondary user uniquely associated with the second communication device 140. In an embodiment, where the secondary communication device 140 is adapted to receive contextual information in accordance with the primary user of the first communication device 110, the secondary user has to be authenticated using the access details of the primary user itself and/or authorized to use the contextual information received from the primary device.

In some embodiments, the second authentication module 176 may be associated to a corresponding module onto the backend server 150 so as to authorize the secondary user an access onto the second application 160 of the second communication device 140. The authentication module 176 is generally adapted to be executed in collaboration with the second graphical user interface 161 so as to enable the secondary user to communicate there through. In a preferred embodiment, the second graphical user interface 161 comprises an authenticating form (not shown), adapted to receive one or more inputs from the secondary user. Such an authenticating form may require the primary user to fill authentication information therein. The authentication information, may be in accordance with one or more authentication methods selected from but not limited to a combination of login ID/email ID/user ID/device ID and a password; one or more biometric measurement (including fingerprints, facial and/or eye feature matching); and/or a pattern to be designed onto the first communication device and/or security questions; one-time password (OTP) tokens (e.g., as generated in conjunction with an email/phone number of the registered user); and/or any conventionally known authenticating/identifying mechanism known and any possible combinations thereof.

The authentication module 176 further includes a control mechanism adapted to set one or more user profiles, authentication methods/login identifiers to enable access parameters, privileges, level of permissions, device type/identifier, and the like for enabling the secondary user to access the second application 140. However, in some embodiments, access may be provided automatically by authenticating the second communication device 140 without a need of the user providing an input for the authentication.

In an embodiment, the authentication module 176 sends over the authentication information to the backend server 150, which in turn validates/disallows the identification/authorization and automatically retrieves device information/user profile/settings, and the like, corresponding to the primary user.

In some embodiments, the process of authentication may be used to provide consent of the primary user to allow various sub-applications 170 of the second application 160, to be executed as required, such that the receiving and/or visualization of one or more context data and/or data streams from the backend server 150 is authorized by the primary user. However, in some instances, such a permission is received from the primary user during the installation of the second application 160 onto the second communication device 140 and is therefore, not required to include such request each time the user logs in the second application 140.

In some embodiments, the control mechanism of the authentication module 176 may be used to configure the type of data streams received thereon. For example, in some preferred instances, the context data is received from the backend server 150. However, in some other instances, the second application 140 receives one or more additional contextual information, related to the information accessed onto the first communication device 140 is received from the backend server 150. In all such instances, the backend server 150 may include additional sub-modules and data sources to determine additional contextual information in relation to the context data received from the first application 120.

Figure 5:
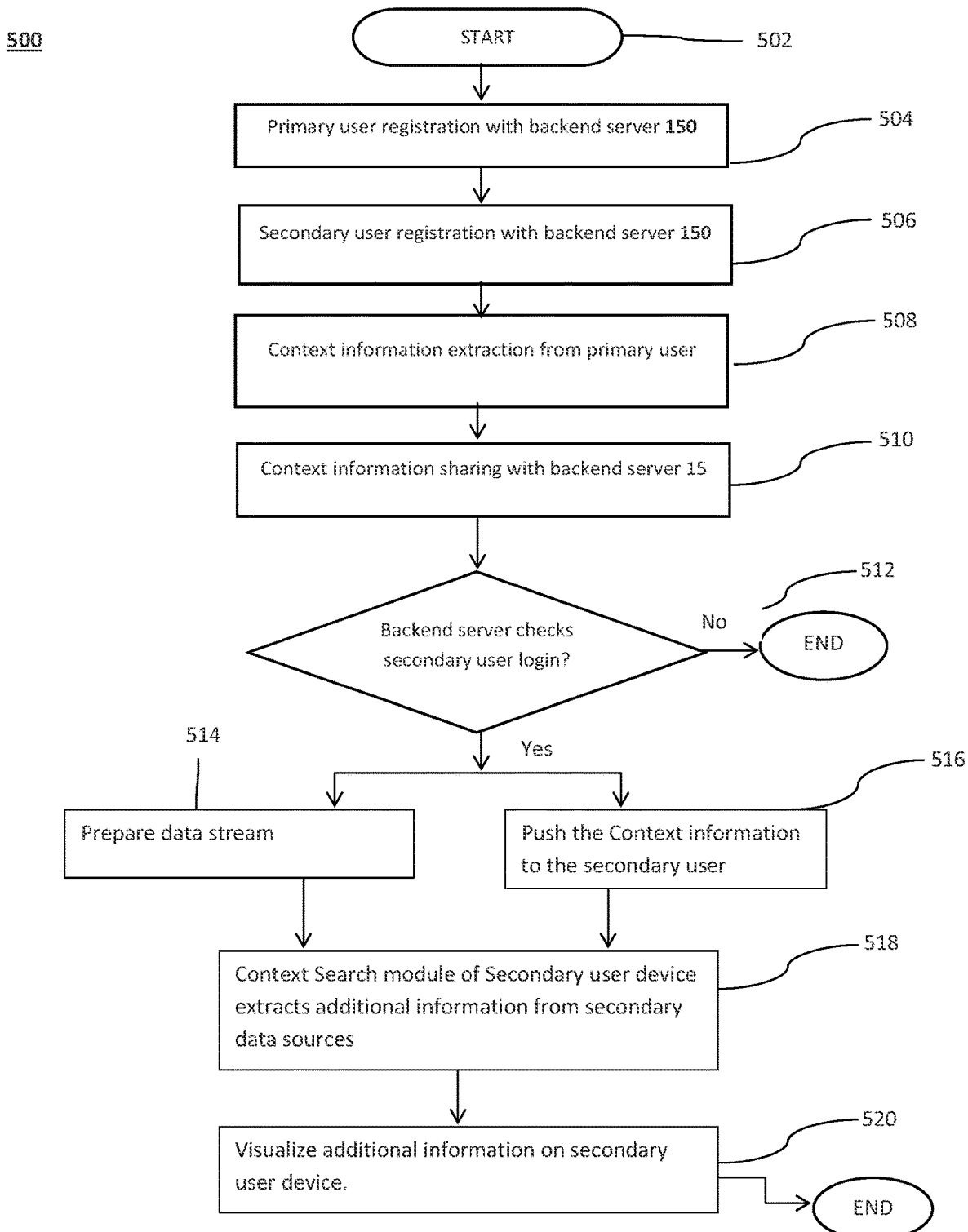
FIG. 5 illustrates a flow chart depicting a method for automatic display of contextually related information between a plurality of communication devices in a real time in accordance with the preferred embodiment of the present subject matter.
Figure 6:
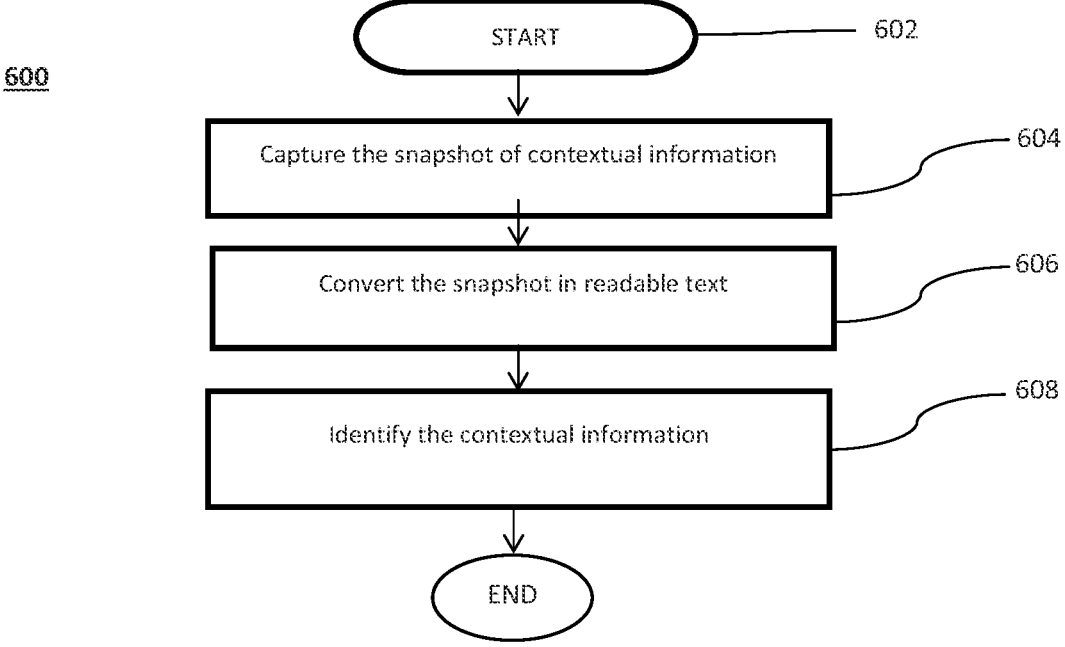
FIG. 6 illustrates a flow chart illustrating a method of determining context data on a primary communication device in accordance with one embodiment of the present subject matter.

In a preferred embodiment, the one or more executable sub-applications 170, include one or more programming instructions that cause a processor of the second communication device 140, utilize one or more resources and/or sub-components and/or sub-programs of the computing device 140, perform one or more predetermined activities and/or process steps (as depicted in FIGS. 5 & 6), as required by the application interface 162. Such predetermined activities and/or process steps may be performed automatically in response to executable instructions from the corresponding executable sub-applications 170 without the direct initiation of the activity by the user. However, in some other embodiments, such predetermined activities and/or process steps may be performed, wholly or partially in response to the primary user's command. In some embodiments, it is to be contemplated that the second application 160, in addition to the disclosed executable sub-applications 170 may also include one or more computer programs, software services, or routines, adapted to operate on the second communication device 140. Further, such programs/services/routines may be able to work in a standalone manner and/or may further be supported by other programs/applications that run on the second communication device 140 and are supported by operating system thereof.

Referring back to FIG. 2, the backend server 150 is generally a computing unit that operates in a computer network 200 by using logical connections to one or more first communication devices 110, and one or more secondary communication devices 140. In some preferred embodiments, the computer network 200 may be a WAN networking environment where each of the backend server 150, the one or more first communication devices 120, and the one or more secondary communication devices 140, might comprise a modem or other means for establishing communications over the WAN, such as the Internet. However, in other embodiments, the computer network 200 may be in the form of any known network such as a local area networks (LANs) and other networking environments that are commonplace in hospitals, enterprise-wide computer networks, intranets, and the Internet. It will be appreciated by those of ordinary skill in the art that the network connections shown are exemplary and other means of establishing a communications link between the computers (e.g., backend server 150, and the communication devices 120, 140) might be utilized.

In an embodiment, the backend server 150 includes therein, or otherwise has an access thereto a central repository 155, including the plurality of data sets 114 and/or data sets 144 and/or any additional data sets 154 of similar contextual information available thereat. In some embodiments, the central repository 155 may be available on a server memory including but not limited to RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information, and which may be accessed by the backend server 150. However, in other embodiments, the central repository 155 is remote from the backend server 150 and is in the form of a cloud based data store, which may be accessed by the backend server 150 using internet.

The backend server 150 is generally but not necessarily a multi-agent operating system based computing device which receives, processes and sends a data stream in the form of context data and/or an additional contextual information authorized to be shared between multiple communication devices i.e., the one or more first communication devices 120, and the one or more second communication devices 140, in real time. Accordingly, the first communication devices 120, as well as the second communication devices 140, has to be pre-authorized by the primary user for enabling a real time data stream sharing through the backend server 150.

The backend server 150 includes one or more executable sub-applications 180. In an embodiment, the executable sub-applications include a context receiving sub-application 181, a data-stream preparation sub-application 182, an information pushing sub-application 183, and an access manager sub-application 186. However, it is to be contemplated that one or more other sub-application as desired, and necessary to provide any of the aforementioned features/functionalities may also be present without deviating from the scope of the current disclosure.

As can be understood from the name, the context receiving sub-application 181 is a module that is adapted to allow receiving of one or more contexts from the first communication device 110 onto the backend server 150.

The data-stream searching sub-application 172 is a module adapted to at least partially combine the one or more context data received from the first application 110 and/or automatically search the one or more of the central repository 155 and/or the first data sources 115 and/or second data sources 145, for additional contextual information related to the contexts to be shared with the second communication device 140. The additional contextual information is searched in accordance with a user role/schema/profile of the secondary user. For example, when a context received is a patient ID from a patient health record, at the secondary device 140, of a laboratory—the additional data that is searched for, may be various lab reports, sample details, and the like relevant to the user profile i.e., laboratory.

The context pushing sub-application 183 is a module adapted to push the data-stream identified at the backend server 150 for the secondary user of a predetermined second communication device 140. The communication between the sub-application 183 of the backend server 150 and the second communication device 140 may use one or more communication means connecting the second device 140 and the backend server 150. In other embodiments, the communication channel may include one or more REST (Representational State Transfer) API adapted to automatically push the data-streams from the memory/storage of the backend server 150. In yet other embodiments, any known suitable means/methods of sharing information between an application and a backend server may be utilized.

The access management module 186 of the backend server 150 is adapted to work in collaboration with the first authentication modules 136 of a plurality of the first communication devices 110 and the second authentication modules 176 of a plurality of the second communication devices 140. In an embodiment of the present invention, the access management module 186 may be adapted to identify and/or authenticate a primary user who is uniquely associated with at least one of the first communication device 110 and the secondary communication devices 140 such that a data stream may be shared in real time with the one or more secondary devices 140, in accordance with one or more contextual information accessed onto the first communication device 110.

Particularly, the access management module 186 is adapted to receive authentication information from each of the first communication devices 110, and each of the second communication devices 140. Once received, the authentication information is compared against a pre-stored authentication data of each of the users, within the memory of the backend server.

Thereafter, the access management module 186 in accordance with the primary user, forms a network of the devices between which information may be shared. Further, the access management module 186 is also configured to update the rule engine 157 in accordance with the authentication configuration/settings of the primary users for each of the primary devices 110 and/or secondary device 140. In some embodiments, each of the secondary device 140 is configured to receive only a predetermined kind of context and/or information, for example, a secondary user working in a laboratory may receive a lab report, a third party doctor may receive diagnosis history, and so on. Similarly, the access manager module 186 is adapted to configure push notification parameters for each of the secondary device 140, and so on.

In a preferred embodiment, one or more executable sub-applications 180, include one or more programming instructions that cause a processor of the backend server 150, utilize one or more resources and/or sub-components and/or sub-programs of the computing device, perform one or more predetermined activities and/or process steps (as disclosed in FIGS. 5 & 6). Such predetermined activities and/or process steps may be performed automatically in response to executable instructions from the corresponding executable sub-applications 180 without user direct initiation of the activity. However, in some other embodiments, such predetermined activities and/or process steps may be performed, wholly or partially in response to the primary user's command. In some embodiments, it is to be contemplated that the backend application 158, in addition to the disclosed executable sub-applications 180 may also include one or more computer programs, software services, or routines, adapted to operate on the backend server 150. Further, such programs/ services/routines may be able to work in a standalone manner and/or may further be supported by other programs/ applications that run on the backend server 150 are supported by operating system thereof.

In an embodiment, the backend server 150 is adapted to receive the one or more context data 125 from the first application interface 122, which is then processed to create one or more data-streams 165, in accordance with a predetermined rule engine 157 by using one or more of patient healthcare data sets 114 and/or second data sets 144 and/or additional data sets 154 of the central repository 155, and shares/pushes towards the one or more second application interface 162 of the predetermined second communication devices 140.

In a preferred embodiment, the data stream 165 includes the one or more context data 125 received from the primary user, at least partially combined together by the backend server 150. In such a case, the data stream 165 is utilized at the secondary communication device 140 to discover additional contextual information from within the data sets 144 of the second data sources 145 in accordance with the rule engine 157. Such additional contextual information is then visualized automatically on the GUI of the secondary communication device 140. However, in other embodiments, the data stream 165 may include one or more additional contextual information prepared by the backend server 150 by utilizing the context data 125, and searching one or more of the data sources 115, 145 and 155 for any relevant contextual information in accordance with the rule engine 166. In such instances, the data stream 165 is directly visualized on the GUI of the secondary communication device 140 without having to look for any additional information. The additional contextual information to be visualized onto the secondary communication devices 140 is generally dependent on a device profile which in turn is utilized along with rule engine 157 so as to visualize only a relevant contextual information related to the contextual information accessed onto the first communication device 110, and that too in a real time such that both the devices 110, 140 may work in a collaboration at the same time.

Figure 3:
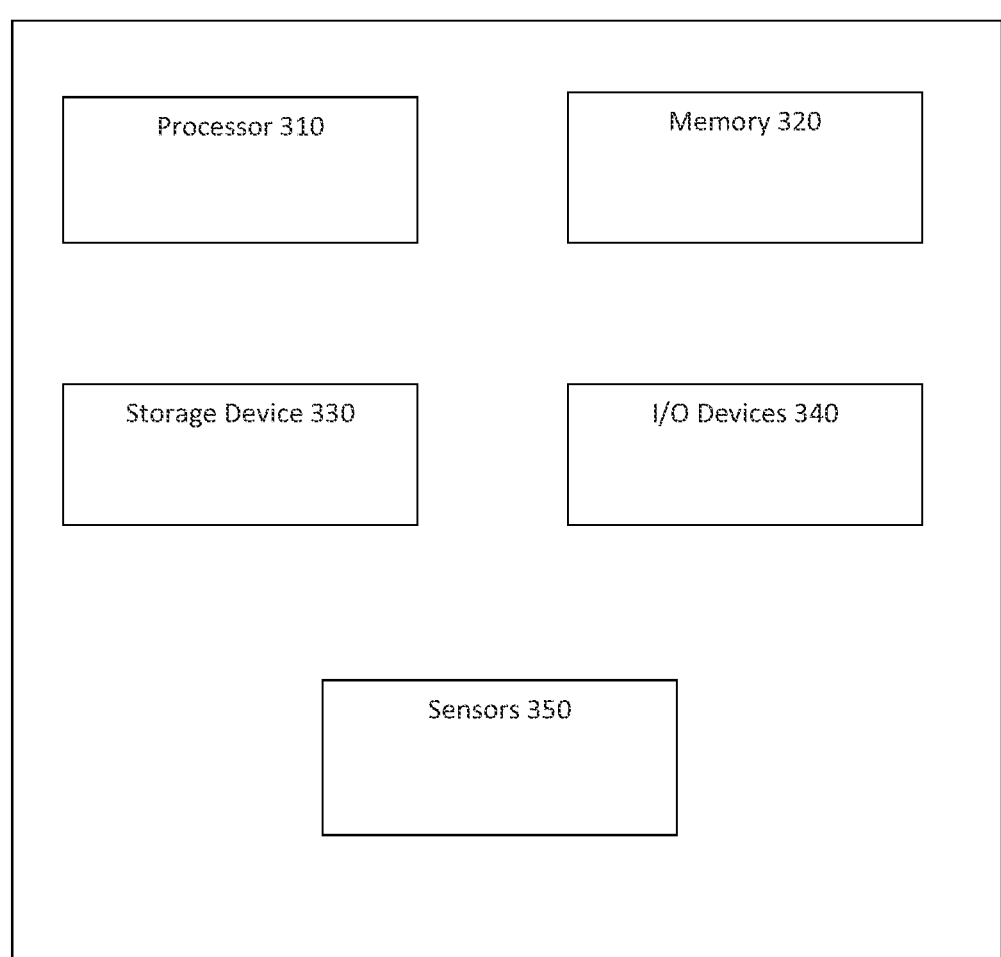
FIG. 3 illustrates an exemplary communication device in accordance with one embodiment of the present subject matter.

The communication devices 110, 140 are generally intended to represent various forms of computing units such as mobile devices, including personal digital assistants, cellular telephones, smart phones, tablets, laptops, workstations, and other similar computing units as illustrated in FIG. 3. The components shown here, their connections and relationships, and their functions, are meant to be exemplary only, and are not meant to limit implementations described and/or claimed in this document. In a preferred embodiment, as illustrated in FIG. 3, a computing unit 300 includes a processor 310, memory 320, a storage device 330, a high-speed interface connecting to memory and high-speed expansion ports, and a low speed interface connecting to low speed bus, one or more input/output (I/O) devices 340 and a plurality of sensors 350. Each of the components 310, 320, 330, 340, 350 are interconnected using various busses, and may be mounted on a common motherboard or in other manners as appropriate. The processor 310 can process the programming instructions for execution within the system 100. In a preferred embodiment, the programming instructions may be stored in the memory 320 or on the storage device 330 to display graphical information for a GUI on an external input/output device 340, such as display coupled to high speed interface. In other implementations, multiple processors and/or multiple busses may be used, as appropriate, along with multiple memories and types of memory.

Processor 310 may communicate with a user through control interface (not shown) and display interface coupled to a display. The display may be, for example, a TFT LCD (Thin-Film-Transistor Liquid Crystal Display) or an OLED (Organic Light Emitting Diode) display, or other appropriate display technology. The display interface may comprise appropriate circuitry for driving the display to present graphical and other information to a user. The control interface may receive commands from a user and convert them for submission to the processor 310. In addition, an external interface may be provided in communication with processor 310, so as to enable near area communication of the computing unit 300 with other devices. External interface may provide, for example, for wired communication in some implementations, or for wireless communication in other implementations, and multiple interfaces may also be used.

The computing unit 300 is shown as including the memory 320. The memory 320 may store the executable programming instructions of the application interface 122. The executable instructions of the application interfaces 122, 162 and/or the sub-applications 130, 170 may be stored or organized in any manner and at any level of abstraction, such as in connection with one or more applications, processes, routines, procedures, methods, functions, etc.

In one implementation, the memory 320 is a volatile memory unit or units. In another implementation, the memory 320 is a non-volatile memory unit or units. The memory 320 may also be another form of computer-readable medium, such as a magnetic or optical disk. In one implementation, a computer program product is tangibly embodied in an information carrier. The computer program product contains instructions that, when executed, perform one or more methods, such as those described above. The information carrier is a computer- or machine-readable medium, such as the memory, expansion memory, or memory on processor.

Expansion memory may also be provided and connected to the computing unit 300 through the expansion interface, which may include, for example, a SIMM (Single In Line Memory Module) card interface. Such expansion memory may provide extra storage space for the computing unit 300 or may also store applications or other information for the computing unit 300. In an embodiment, expansion memory may include instructions to carry out or supplement the processes described above and may include secure information also. Thus, for example, expansion memory may be provided as a security module for computing unit 300 and may be programmed with instructions that permit secure use of computing unit 300. In addition, secure applications may be provided via the SIMM cards, along with additional information, such as placing identifying information on the SIMM card in a non-hackable manner. The instructions stored in the memory 320 may be executed by one or more processors, such as a processor 310. The processor 310 may be coupled to one or more input/output (I/O) devices 340.

The storage device 330 is capable of providing mass storage for the computing unit 300. In one implementation, the storage device 330 may be or contain a computer-readable medium, such as a floppy disk device, a hard disk device, an optical disk device, a tape device, a flash memory or other similar solid state memory device, or an array of devices, including devices in a storage area network or other configurations.

A computer program product can be tangibly embodied in an information carrier. The computer program product may also contain instructions that, when executed, perform one or more methods, such as those described above. The information carrier is a computer- or machine-readable medium, such as the memory 320, the storage device 330, or memory on processor 310.

In some embodiments, the I/O device(s) may include one or more of a keyboard or keypad, a touchscreen or touch panel, a display screen, a microphone, a speaker, a mouse, a button, a remote control, a joystick, a printer, a telephone or mobile device (e.g., a smartphone), a sensor, etc. The I/O device(s) may be configured to provide an interface to allow a user to interact with the computing unit 300.

In an embodiment, the memory 320 may include a central repository 155 for storing data received from the plurality of corresponding data sources 115/145. The central repository 155 furthermore store details on complete incident and event log that clearly shows incident types, incident types, actions taken when incidents happen—all in a nice, visualized format.

The computing unit 300 may communicate wirelessly through communication interface, which may include digital signal processing circuitry where necessary. Communication interface may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver.

The computing unit 300 may also communicate audibly using audio codec, which may receive spoken information from a user and convert it to usable digital data set 114, 144. Audio codec may likewise generate audible sound for a user, such as through a speaker, e.g., in a handset of the computing unit 100. Such sound may include sound from voice telephone calls, may include recorded sound (e.g., voice messages, music files, etc.) and may also include sound generated by applications operating on computing unit 300.

Additionally, the computing unit 300 may include Universal Serial Bus (USB) flash drives. The USB flash drives may store operating systems and other applications. The USB flash drives can include input/output components, such as a wireless transmitter or USB connector that may be inserted into a USB port of another computing unit.

The computing unit 300 is illustrative. In some embodiments, one or more of the entities may be optional. In some embodiments, additional entities not shown may be included. For example, in some embodiments the system 100 may be associated with one or more networks. In such embodiments, the entities may be arranged or organized in a manner different from what is shown in FIG. 1.

The backend server 150 is generally to the computing unit 300 as explained above. However, it may include one or more additional components, which provides it with additional utilities/functionalities required for the purpose of a backend server/application. Such components/utilities/functionalities are already well known in the art and therefore does not need any further elaborations.

FIG. 4 illustrates various examples of additional contextual information, in accordance with different embodiments of the present subject matter. As illustrated, when a patient is searched on a first application installed onto the first computing device, the contextual data, such as Name and Date of Birth, are utilized to display one or more additional contextual information onto other applications on various second computing devices. For example, as illustrated, patient vitals on to a second application on a device no. 2, medication orders onto a third application installed within a device no. 3, allergy information onto a fourth application installed within a device no. 4, and lab results onto a fifth application installed within a device no. 5. However, in other embodiments, the additional contextual information may include one or more of but not limited to various aspects of the patient state, including patient vitals, lab results, medication orders, diagnosis codes, condition codes, clinical orders, indexed values from clinical notes or other text documents, patient demographic information, patient history, patient images, and a variety of other patient information, which may be utilized for the purpose of determining any underlying patient information for optimizing the diagnosis and/or treatment.

FIG. 5 illustrates a flow chart of a method 500 for automatic display of contextually related information between a plurality of communication devices in a real time in accordance with the preferred embodiment of the present subject matter in accordance with FIG. 1 through FIG. 4 as disclosed earlier. Particularly, the method is directed towards sharing one or more context data related to a patient healthcare information. The method starts at step 502 and proceeds to step 504.

At step 504, a user registers itself with the backend server 150 through a primary application 121 installed onto a first communication device 110 as a primary user, thereby authorizing the backend server 150 to receive one or more context data therefrom, when a contextual information such as a Patient EMR, PHR is accessed thereon the first communication device 110.

The method further includes step 506 where one or more other users register themselves with the backend server 150, each user registering through a different secondary application 140 installed onto a different secondary communication device 140 as a secondary user, thereby subscribing to receive in real time, one or more context data from the primary application 120 of the primary user, and therefore authorizes the backend server 150 to push one or more data-streams including one or more context data related to a contextual information accessed onto the primary device 110 of the predetermined primary user. In an embodiment, the context-data in case of patient health record may include Patient ID, Date of Birth, Date of Treatment, and the like, which may be utilized to find additional related contextual information at the secondary communication device 140 in accordance with a role and/or profile and/or utility of the secondary user.

In some embodiments, of the present invention, the primary application 120 may be able to subscribe as a secondary application for a third primary application associated to the same and/or different primary user and installed onto a third communication device (not shown). In such embodiments, the same first application 120 installed onto the first communication device 110 acts as a primary application for one or more secondary applications 160 installed onto the one or more secondary devices 140, and therefore sends contexts to the backend server 150 to be shared with such secondary devices 140. Additionally, in such embodiments, the same first application 120 is also adapted to receive one or more data streams including context data from the backend server 150 in accordance with the information accessed onto the third communication device and received therefrom. In all such embodiments, the application 120 includes all the sub-applications modules 160 integrated therein, which may be accessed onto the basis of role i.e., whether the user is logged in as a primary user or a secondary user.

Preferably, the steps 504 and 506 may be performed sequentially in an order as described. However, in some instances, they may also be performed in parallel, but the step 506 may not be performed before the step 504.

The method then proceeds to step 508 where, whenever a contextual information such as a patient healthcare record, for example an EMR, PHR, Lab Report, Diagnosis report, and the like as already disclosed earlier, is accessed onto the first communication device 110, a context data such as a patient ID, date of birth, and the like, is determined and sent over to the backend server 150.

Such a method of determination of context is elaborated and illustrated in the flow chart of FIG. 6. The method starts at step 602 and proceeds to step 604 where an access detection sub-application determines an access of the one or more contextual information onto the first communication device 110. Thereafter, the method proceeds to step 606 where the screenshot taken at previous step is recognized by using the recognition sub-application to convert the image in the form of parse able and/or readable text/objects and the like. The method then proceeds to step 608 where the recognized text/objects are parsed out using one or more context determination models to determine one or more context data/elements, which may be utilized to identify the contextual information accessed onto the first communication device 110.

Looping back to the method 500, the method proceeds to step 510 where the context data determined at the previous step is shared and/or communicated to the backend server 150 through the context sharing sub-application 135 as disclosed earlier where it is optionally secured in a memory and/storage device thereof in accordance with the primary user/predetermined schema, role, and the like. However, in some embodiments, the context determination sub-application 134 is not present within the first application 120. In such embodiments, the screenshot taken by the capturing sub-application 132 may be considered as an output to be shared at the next step.

Once the context data 125 is received at the backend server 150, the backend server, at step 512 checks if one or more secondary user of the secondary applications 160 corresponding to the primary application 120 is logged in and/or active. If, in response to check at step 512, it is determined that no secondary user and/or secondary application is active at the moment, the method does nothing and comes to an end.

If, however, response is yes, the backend server 150 moves to step 514, prepares a data stream 190 in accordance with the user profile of the active secondary users/applications 160. In some embodiments, the data stream 190 is prepared by optionally determining the context, particularly in cases where only the captured screenshot is shared with the backend server 150, without determining the context data followed by combining at least partially the context data 125 received from the primary application 120 and pushing towards the secondary application 160 where it is notified and/or received by the data stream receiving/notification sub-application 171 at step 516. Thereafter, the method proceeds to step 518 where the contextual information searching sub-application 172 looks into the one or more second data sources 145 and tries to find out additional contextual information related to the context data 125 received thereat. For example, if the secondary device 160 belongs to a user of laboratory, the additional information that would be searched for is lab reports and/or other vitals/tests report for the patient as determined by the context received. Once the additional contextual information is determined, the method proceeds to step 520 where the visualization sub-application 173 visualizes the related contextual information determined at the previous step, onto the GUI 161 of the secondary application 160.

However, in other embodiments, the method after the step 512 moves to the step 515 where the data stream 190 is prepared by searching for additional contextual information relevant within one or more of central repository 155, the one or more first data sources 115 and/or the one or more secondary data sources 145 in accordance with the user profile of the secondary application 160 and pushed the same towards the secondary application 160 at step 517 and visualized directly at step 520.

FIGS. 5 and 6 illustrate an exemplary embodiment of the present invention. It is understood that various features, sub-combinations, and modifications of the embodiments described herein are of utility and may be employed in other embodiments without reference to other features or sub-combinations. Moreover, the order and sequences of steps shown in the example methods 500 and 600 are not meant to limit the scope of the present disclosure in any way, and in fact, the steps may occur in a variety of different sequences within embodiments hereof. Such variations and combinations thereof are also contemplated to be within the scope of embodiments of this disclosure.

Various connections are set forth between elements in the description and in the drawings (the contents of which are included in this disclosure by way of reference). These connections in general and, unless specified otherwise, may be direct or indirect and that this specification is not intended to be limiting in this respect. In this respect, a coupling between entities may refer to either a direct or an indirect connection.

Various embodiments of the invention have been disclosed. However, it should be apparent to those skilled in the art that modifications, in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

In an embodiment, the method and system, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements, e.g., pre-determined level of one or more parameters of gases as declared by government. The storage elements may also hold data or other information, as desired. The storage element may be in the form of an information source, or a physical memory element present in the processing machine.

The programmable or computer-readable instructions may include various commands that instruct the processing machine to perform specific tasks, such as steps that constitute the method of the disclosure. The systems and methods described can also be implemented by using only software programming or using only hardware or by a varying combination of the two techniques. The disclosure is independent of the programming language and the operating system used in the computers. The instructions for the disclosure can be written in all programming languages including, but not limited to, "C," "C-HE," "Visual C-HE," Java, and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various implementations of the systems and techniques described here can be realized in digital electronic circuitry, integrated circuitry, especially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

The systems and techniques described here can be implemented in a computing system that includes a backend component (e.g., as a data server), or that includes a middleware component (e.g., an application server), or that includes a front end component (e.g., a client computer having a graphical user interface or a Web browser through which a user can interact with an implementation of the systems and techniques described here), or any combination of such backend, middleware, or front end components. The components of the system can be interconnected by any form or medium of digital data communication (e.g., a communication network). Examples of communication networks include a local area network ("LAN"), a wide area network ("WAN"), and the Internet.

The claims can encompass embodiments for hardware, software, or a combination thereof.

Although a few implementations have been described in detail above, other modifications are possible. Moreover, other mechanisms for performing the systems and methods described in this document may be used. In addition, the logic flows depicted in the figures may not require the particular order shown, or sequential order, to achieve desirable results. Other steps may be provided, or steps may be eliminated, from the described flows, and other components may be added to, or removed from, the described systems. Accordingly, other implementations are within the scope of the following claims.

I claim:

1. A method for automatic display of contextually related information between a plurality of communication devices in real-time, the method comprising:

determining one or more context data related to a predetermined contextual information of a predetermined information type on a first application interface installed in a first communication device;

communicating the one or more context data related to the predetermined contextual information from the first application interface to a backend server;

preparing a data stream by the backend server on a basis of the one or more context data determined by at least one executable sub-application of the first application interface, the at least one executable sub-application automatically detecting, capturing and recognizing an access of the predetermined contextual information of the predetermined information type on the first communication device, and combining at least a portion of the one or more context data received from the first communication device in real-time, wherein the data stream comprises one or more additional contextual information related to the information accessed on the first device;

receiving, in real-time, the data stream related to the predetermined contextual information at one or more subscribed second application interfaces installed within one or more second communication devices; and discovering the additional contextual information from at least one data set accessed by the backend server, wherein the at least one executable sub-application:

detects activity of one or more predefined processes on the first communication device;

captures a screenshot of a screen on detection of activity of the one or more predefined processes on the first communication device;

recognizes a dataset having at least one of text and objects from the captured screenshot;

determines a context of the dataset using at least one determination learning model;

utilizes a time stamp associated with the dataset, the time stamp stored in a memory of the first communication device, to ensure receiving, in real-time, the data stream related to the predetermined contextual information at the one or more subscribed second application interfaces installed within one or more second communication devices; and processes the captured screenshot via a recognizing unit to determine the one or more predetermined contextual information on the first communication device.

2. The method of claim 1, wherein the one or more predetermined contextual information comprises a patient healthcare data selected from one or more of: a Patient EMR, PHR, X-ray, lab-reports, or a diagnosis.

3. The method of claim 2, wherein the one or more context data is an identifier selected from one or more of: a patient ID, a date of birth, gender, mobile number, or social security number (SSN).

4. The method of claim 1, wherein the recognizing unit comprises one or more programs selected from: an OCR Program, Image Matching program, or video detection.

5. A computerized system for sharing patient records on a plurality of communication devices, the system comprising:

a first communication device comprising a first application interface adapted to communicate with a backend server, the first communication device comprising one or more first data sources comprising a plurality of a first contextual information in a form of patient health record data; and one or more second communication devices, each of the one or more second communication devices comprising a second application interface, wherein each second application interface is adapted to receive one or more data streams related to one or more designated patients, from the backend server, wherein the one or more second communication devices comprise one or more second data sources comprising a plurality of a second contextual information in a form of patient health record data, the data stream being prepared by the backend server on a basis of one or more of the first contextual information related to at least one EMR of the patient from the first application interface, wherein the first contextual information is automatically detected, captured and recognized in real-time by at least one executable sub-application of the first application interface automatically when one or more predetermined type of record is accessed on the first communication device, wherein the data stream comprises one or more additional contextual information related to the information accessed on the first communication device, and wherein the additional contextual information is discovered from at least one data set accessed by the backend server, wherein the at least one executable sub-application:

detects activity of one or more predefined processes on the first communication device;

captures a screenshot of a screen on detection of activity of the one or more predefined processes on the first communication device;

recognizes a dataset having at least one of text and objects from the captured screenshot;

determines a context of the dataset using at least one determination learning model;

utilizes a time stamp associated with the dataset, the time stamp stored in a memory of the first communication device, to ensure receiving, in real-time, the data stream related to the predetermined contextual information at the one or more subscribed second application interfaces installed within one or more second communication devices; and processes the captured screenshot via a recognizing unit to determine the one or more predetermined contextual information on the first communication device.

6. A computerized system having a non-transitory computer-readable medium storing instructions, the instructions comprising:

one or more instructions that, when executed by one or more processors, cause the one or more processors to:

determine one or more context data related to at least one contextual information accessed on a first device using a first application interface installed within a first communication device, the first communication device communicating the one or more context data from the first application interface to a backend server;

receive, in real-time, a data stream related to one or more subscribed second application interfaces installed within one or more second communication devices;

prepare the data stream by the backend server on a basis of one or more context data received from the first application interface, wherein the context data is automatically determined by at least one executable sub-application of the first application interface in real-time by detecting, capturing, and recognizing one or more access of the contextual information on the first communication device, wherein the data stream comprises one or more additional contextual information related to the contextual information accessed on the first device; and discover the additional contextual information from at least one data set accessed by the backend server, wherein the at least one executable sub-application:

detects activity of one or more predefined processes on the first communication device;

captures a screenshot of a screen on detection of activity of the one or more predefined processes on the first communication device;

recognizes a dataset having at least one of text and objects from the captured screenshot;

determines a context of the dataset using at least one determination learning model;

utilizes a time stamp associated with the dataset, the time stamp stored in a memory of the first communication device, to ensure receiving, in real-time, the data stream related to the predetermined contextual information at the one or more subscribed second application interfaces installed within one or more second communication devices; and processes the captured screenshot via a recognizing unit to determine the one or more contextual information on the first communication device.

7. The computerized system of claim 6, wherein the at least one contextual information comprises a patient healthcare data selected from one or more of: a Patient EMR, PHR, X-ray, lab-reports, and/or a diagnosis; and, wherein the one or more context data is an identifier selected from one or more of: a patient ID, a date of birth, gender, mobile number, and/or social security number (SSN).

8. The computerized system of claim 6, wherein the recognizing unit comprises one or more programs selected from: an OCR Program, Image Matching program, and/or video detection.

* * * * *